US00PP16457P2

(12) United States Plant Patent
Smith

(10) Patent No.: US PP16,457 P2
(45) Date of Patent: Apr. 18, 2006

(54) ***ASTER* PLANT NAMED 'YOBELIEVER'**

(50) Latin Name: *Aster hybrida*
Varietal Denomination: Yobeliever

(75) Inventor: Mark A. Smith, Fort Myers, FL (US)

(73) Assignee: Yoder Brothers, Inc., Barberton, OH (US)

( * ) Notice: Subject to any disclaimer, the term of this patent is extended or adjusted under 35 U.S.C. 154(b) by 56 days.

(21) Appl. No.: 11/045,988

(22) Filed: Jan. 28, 2005

(51) Int. Cl.
*A01H 5/00* (2006.01)

(52) U.S. Cl. ..... Plt./355

(58) Field of Classification Search ..... Plt./355
See application file for complete search history.

*Primary Examiner*—Kent Bell
(74) *Attorney, Agent, or Firm*—C. A. Whealy

(57) ABSTRACT

A new and distinct cultivar of *Aster* plant named 'Yobeliever', characterized by its uniform, outwardly spreading and mounded plant habit; freely branching growth habit; dark green-colored foliage; uniform flowering habit; natural flowering season around September $4^{th}$ ; daisy-type inflorescences with dark violet blue-colored ray florets; and good garden performance.

1 Drawing Sheet

Botanical designation: *Aster hybrida.*
Cultivar denomination: 'Yobeliever'.

BACKGROUND OF THE INVENTION

The present Invention relates to a new and distinct cultivar of *Aster* plant, botanically known as *Aster hybrida* and hereinafter referred to by the name 'Yobeliever'.

The new *Aster* is a product of a planned breeding program conducted by the Inventor in Leamington, Ontario, Canada and Alva, Fla. The objective of the program is to develop new potted *Aster* cultivars that have a uniform plant growth habit, good vigor and strong branching habit, numerous inforescences, desirable inflorescence form and floret colors, uniform flowering response and good postproduction longevity.

The new *Aster* originated from an open-pollination made by the Inventor during the fall of 1999, in Leamington, Ontario, Canada, of the *Aster hybrida* cultivar Judith, not patented, as the female, or seed, parent with an unknown *Aster hybrida* selection, not patented, as the male, or pollen, parent. The new *Aster* was discovered and selected by the Inventor in January, 2001, as a single flowering plant from within the resulting progeny of the stated open-pollination grown in a controlled environment in Alva, Fla.

The selection of this plant was based on its uniform plant growth habit, good vigor and strong branching habit, numerous inflorescences, desirable inforescence form and floret colors, uniform flowering response and good postproduction longevity.

Asexual reproduction of the new *Aster* by vegetative tip cuttings was first conducted in Alva, Fla. in March, 2001. Asexual reproduction by cuttings has shown that the unique features of this new *Aster* are stable and reproduced true to type in successive generations.

SUMMARY OF THE INVENTION

The cultivar Yobeliever has not been observed under all possible environmental conditions. The phenotype may vary somewhat with variations in environment such as temperature, daylength, and/or light level, without, however, any variance in genotype.

The following traits have been repeatedly observed and are determined to be the unique characteristics of 'Yobeliever'. These characteristics in combination distinguish 'Yobeliever' as a new and distinct cultivar of *Aster*:

1. Uniform, outwardly spreading and mounded plant habit.
2. Freely branching growth habit.
3. Dark green-colored foliage.
4. Uniform flowering habit.
5. Natural flowering season around September $4^{th}$.
6. Daisy-type inforescences with dark violet blue-colored ray florets.
7. Good garden performance.

Plants of the new *Aster* can be compared to plants of the female parent, the cultivar Judith. In side-by-side comparisons conducted in Alva, Fla., plants of the new *Aster* differed from plants of the cultivar Judith, in the following characteristics:

1. Plants of the new *Aster* were stronger than plants of the cultivar Judith.
2. Plant habit of plants of the new *Aster* was more rounded and more uniform than plant habit of plants of the cultivar Judith.
3. Leaves of plants of the new *Aster* were darker green in color and less susceptible to Powdery Mildew than leaves of plants of the cultivar Judith.
4. Plants of the new *Aster* flowered a few days earlier than plants of the cultivar Judith under natural season conditions.
5. Plants of the new *Aster* had slightly smaller inflorescences than plants of the cultivar Judith.

Plants of the new *Aster* can be compared to plants of the cultivar Purple Viking, disclosed in U.S. Plant Pat. No. 10,357. In side-by-side comparisons conducted in Alva, Fla., plants of the new *Aster* differed from plants of the cultivar Purple Viking in the following characteristics:

1. Plant of the new *Aster* were stronger than plants of the cultivar Purple Viking.
2. Plants habit of plants of the new *Aster* was more rounded and more uniform than plant habit of plants of the cultivar Purple Viking.
3. Plants of the new *Aster* flowered a few days later than plants of the cultivar Purple Viking under natural season conditions.
4. Plants of the new *Aster* had slightly smaller inflorescences than plants of the cultivar Purple Viking.

Plants of the new *Aster* can also be compared to plants of the cultivar Yomagic, disclosed in U.S. Plant Pat. No. 15,690. In side-by-side comparisons conducted in Alva, Fla., plants of the new *Aster* differed from plants of the cultivar Yomagic in the following characteristics:

1. Plants of the new *Aster* flowered a few days later than plants of the cultivar Yomagic under natural season conditions.
2. Plants of the new *Aster* had slightly smaller inflorescences than plants of the cultivar Yomagic.
3. Ray florets of inflorescences of plants of the new *Aster* were lighter in color than ray florets of inflorescences of plants of the cultivar Yomagic.
4. Plants of the new *Aster* were less susceptible to Powdery Mildew than plants of the cultivar Yomagic.

BRIEF DESCRIPTION OF THE PHOTOGRAPHS

The accompanying colored photographs illustrate the overall appearance of the new *Aster* showing the colors as true as it is reasonably possible to obtain in colored reproductions of this type. Colors in the photographs may differ from the color values cited in the detailed botanical description which accurately describe the colors of the new *Aster*.

The photograph at the bottom of the sheet comprises a side perspective view of a typical flowering plant of 'Yobeliever' grown in a container.

The photograph at the top of the sheet comprises a close-up view of typical inflorescences of 'Yobeliever'.

DETAILED BOTANICAL DESCRIPTION

In the following description, color references are made to The Royal Horticultural Society Colour Chart, 1995 Edition, except where general terms of ordinary dictionary significance are used. The aforementioned photographs, following observations and measurements describe plants grown and flowered during the summer in Salinas, Calif., in an outdoor nursey and under conditions which approximate those generally used in commercial potted *Aster* production. During the production of these plants, day temperatures were about 21 to 24° C. and night temperatures were about 10 to 13° C. Two unrooted cuttings were directly stuck in 15-cm containers and exposed to long day/short night conditions for 18 days. After the plants were rooted, plants were exposed to natural season conditions.

Botancial classification: *Aster hybrida* cultivar Yobeliever.

Parentage:

*Female, or seed, parent.*—*Aster hybrida* cultivar Judith, not patented.

*Male, or pollen, parent.*—Unknown *Aster hybrida* selection, not patented.

Propagation:

*Type.*—Terminal vegetative cuttings.

*Time to initiate roots.*—About ten days at 22° C.

*Time to produce a rooted cutting.*—About 16 to 18 days at 22° C.

*Root description.*—Fine, fibrous; white in color, close to 155D.

*Rooting habit.*—Freely branching.

Plant description:

*Appearance.*—Daisy-type potted *Aster*. Upright with lateral branches outwardly spreading; inverted triangle with uniformly mounded crown. Strong and freely branching growth habit with lateral branches potentially developing at every node; dense and full plants. Moderately vigorous.

*Plant height.*—About 28 cm.

*Plant width* (*single plant*).—About 24 cm.

*Lateral branches.*—Length: About 27 cm. Diameter: About 5 mm. Internode length: About 1.1 cm. Strength: Strong. Texture: Smooth, glabrous. Color: 146A.

*Foliage description.*—Arrangement: Alternate; simple; sessile. Length: About 4 cm. Width: About 8 mm. Shape: Linear. Apex: Acute. Base: Attenuate. Margin: Nearly entire with rare minute points. Texture, upper and lower surfaces: Smooth, glabrous. Color: Developing foliages, upper and lower surfaces: 147A. Fully expanded foliage, upper surface: 147A; venation, 147B. Fully expanded foliage, lower surface: Slightly lighter than 147A; venation, 147B.

Inflorescence description:

*Appearance.*—Daisy-type terminal and axillary inflorescences with ligulate to linear-shaped ray florets. Disc and ray florets develop acropetally on a capitulum. Inflorescences not fragrant. Inflorescences face upright to outwardly.

*Flowering response.*—Under natural conditions, plants flower about September 4$^{th}$. Uniform flowering habit.

*Inflorescence longevity.*—Inflorescences maintain good color and substance for about one week on the plant. Inflorescences persistent.

*Quantity of inflorescences.*—Freely flowering habit; about 40 open inflorescences per lateral branch.

*Inflorescence bud.*—Height: About 1 cm. Diameter: About 6 mm. Shape: Oval to elongate. Color: 90A.

*Inflorescence diameter.*—About 2.5 cm.

*Inflorescence height.*—About 1.3 cm.

*Diameter of disc.*—About 8 mm.

*Receptacle diameter.*—About 8 mm.

*Receptacle height.*—About 7 mm.

*Ray florets.*—Shape: Ligulate to linear. Orientation: Initially upright, than about 60 to 75° from vertical. Aspect: Straight, mostly flat. Length: About 1.4 cm. Width: About 2 mm. Apex: Acute. Base: Acute. Marign: Entire. Texture: Smooth, glabrous; satiny. Number of ray florets per inflorescence: About 28 arranged in one or two whorls. Color: When opening, upper surface: Close to 90A. When opening, lower surface: Close to 90D; towards the base, 91B. Fully opened, upper surface: Close to 90A; color does not fade with development. Fully opened, lower surface: Close to 91B.

*Disc florets.*—Arrangement: Massed at center of receptacle. Shape: Tubular, elongated. Apex: Five-pointed. Length: About 6 mm. Diameter, apex: About 2 mm. Diameter, base: Less than 1 mm. Number of disc florets per inflorescence: About 28. Color, immature: Close to 11A. Color, mature: Apex and mid-section: Close to 11B. Base: Close to 157B.

*Phyllaries.*—Quantity per inflorescence: About 20. Length: About 4 mm. Width: About 1 mm. Shape: Ligulate. Apex: Acute. Base: Truncate, fused. Margin: Entire. Texture, upper and lower surfaces: Smooth, glabrous. Color, upper and lower surfaces: 146A.

*Peduncles.*—Length: Terminal peduncle: About 3 cm. Third peduncle: About 4.3 cm. Diameter: Less than 1 mm. Angle to vertical: About 35 to 45° from vertical. Strength: Strong, flexible. Texture: Smooth, glabrous. Color: 146A.

*Reproductive organs.*—Androecium: Stamen quantity per floret: About five. Anther length: About 2 mm. Anther color: 14A. Pollen amount: Scarce. Pollen color: 14A. Gynoecium: Pistil quantity per ray floret: One. Pistil length: About 7 mm. Stigma shape: Bi-parted. Stigma color: 155A. Style length: About 4 mm. Style color: 155A. Ovary color: 157A. Seed/fruit: Seed and fruit production has not been observed.

Disease/pest resistance: Resistance to pathogens and pests common to *Asters* has not been observed on plants grown under commercial production conditions.

Garden performance: Plants of the new *Aster* have been observed to be rain and wind tolerant and to tolerate temperatures from 0 to more than 38° C.

It is claimed:

1. A new and distinct cultivar of *Aster* plant named 'Yobeliever', as illustrated and described.

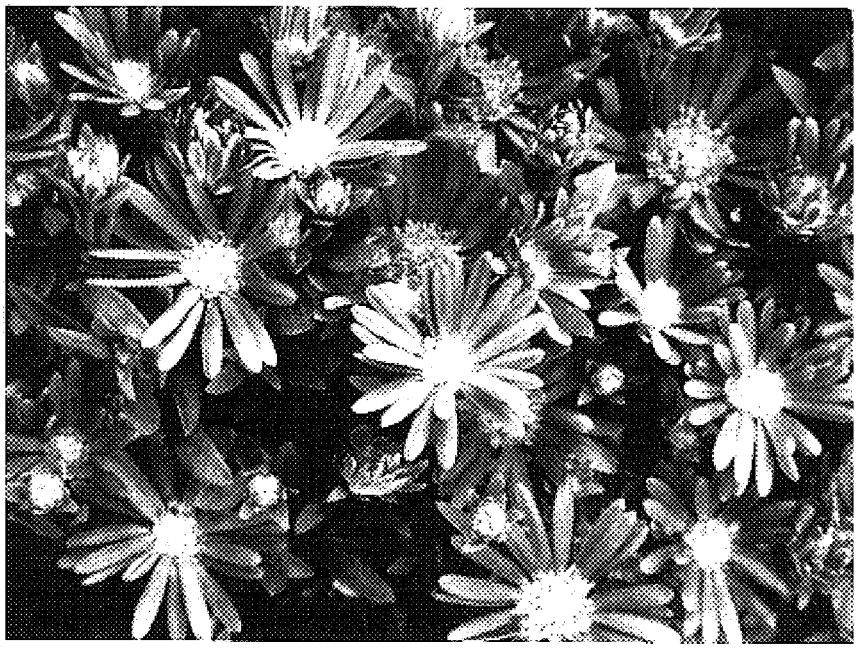
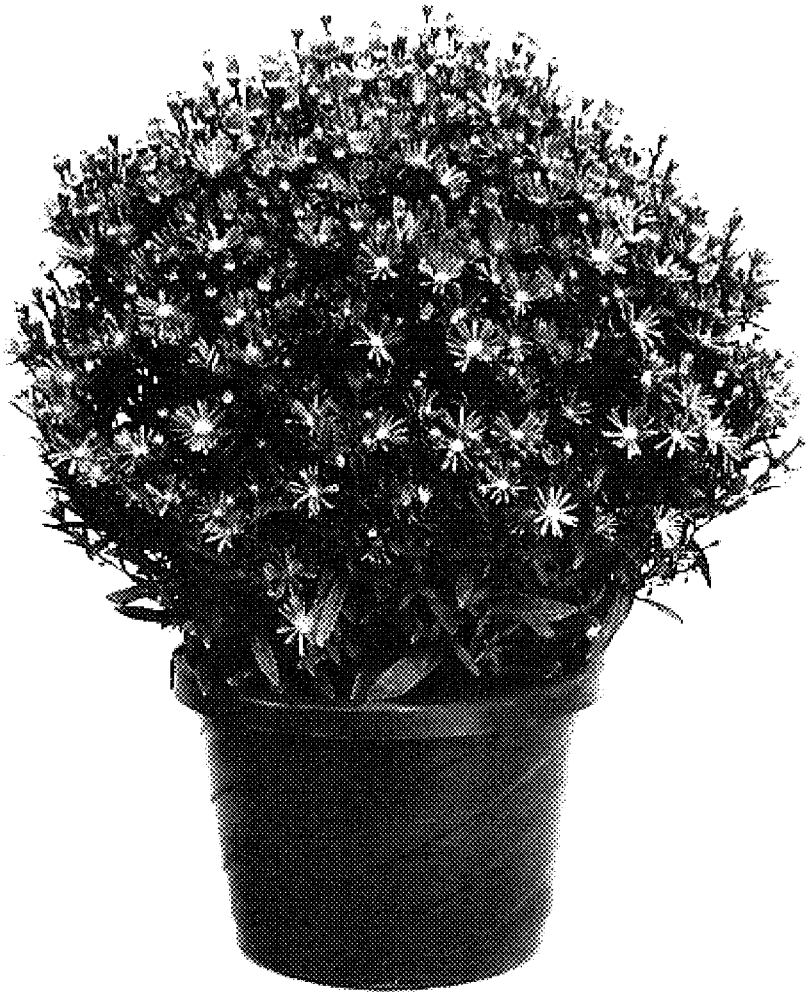

* * * * *